United States Patent [19]

van Gerven

[11] 4,278,090

[45] Jul. 14, 1981

[54] CRYOSURGICAL DEVICE

[75] Inventor: Hans van Gerven, Tübingen, Fed. Rep. of Germany

[73] Assignee: Erbe Elektromedizin KG, Tübingen, Fed. Rep. of Germany

[21] Appl. No.: 56,961

[22] Filed: Jul. 12, 1979

[30] Foreign Application Priority Data

Jul. 15, 1978 [DE] Fed. Rep. of Germany ....... 2831199

[51] Int. Cl.³ .............................................. A61B 17/36
[52] U.S. Cl. .............................. 128/303.1; 62/514 JT
[58] Field of Search ..................... 128/303.1, 399, 400, 128/401; 62/293, 514 JT

[56] References Cited

U.S. PATENT DOCUMENTS

| | | | |
|---|---|---|---|
| 3,272,203 | 9/1966 | Chato | 128/303.1 |
| 3,393,679 | 7/1968 | Crump et al. | 128/303.1 |
| 3,398,738 | 8/1968 | Lamb et al. | 128/303.1 |
| 3,451,395 | 6/1969 | Thyberg | 128/303.1 |
| 3,477,434 | 11/1969 | Hood Jr. et al. | 128/303.1 |
| 3,821,510 | 6/1974 | Muncheryan | 128/395 |
| 4,056,745 | 11/1977 | Eckels | 62/514 JT |
| 4,063,560 | 12/1977 | Thomas et al. | 128/303.1 |

FOREIGN PATENT DOCUMENTS 2422103 5/1974 Fed. Rep. of Germany .
1541099 10/1977 Fed. Rep. of Germany .
2155283 5/1973 France .

OTHER PUBLICATIONS

*Hass,* A Quantitative Hypothermal Method for . . . Injury of Tissue; in Archives of Pathology, vol. 45, #5, May 1948.

*Primary Examiner*—Lee S. Cohen
*Assistant Examiner*—Arthur S. Rose
*Attorney, Agent, or Firm*—Frishauf, Holtz, Goodman & Woodward

[57] ABSTRACT

The invention concerns a cryosurgical instrument with a probe for cooling limited zones of biological tissues, of which the thermally well-conducting tip has a hollow interior cross-section, into which a supply conduit connects with a constricted exit gap, through which a gas for cooling of the tip by means of the Joule-Thomson effect can be supplied by flow through the exit gap and can be led away therefrom through a coaxial discharge conduit open eventually to the atmosphere, the instrument also being provided with a device for control of the temperature of the probe tip.

5 Claims, 2 Drawing Figures

CRYOSURGICAL DEVICE

BACKGROUND OF THE INVENTION

Cryosurgical instruments in which the probe tip is cooled with assistance of the Joule-Thomson effect provided by flow-through of a gas such as laughing gas ($N_2O$) or carbon dioxide ($CO_2$), have in the last few decades found application for surgical purposes with good results (Archives of Pathology, May 1948, Pages 565 and 566). This holds also for other known cryosurgery instruments, in which the probe tip is cooled by vaporization of a liquefied gas.

In the case of cryosurgical instruments of these two kinds, it is further known and common to provide an electrical heating device in the region of the probe tip, that is intended to make possible a quick thawing of the probe (German OS NO. 24 22 103), and which is intended to serve also for temperature control with respect to the cryosurgical instruments utilizing the Joule-Thomson effect, because it is not sufficient in certain cases by adjustment, for example, of the outlet valve of the gas flask to control the supplied gas quantity in such a way that a suitable temperature of the probe tip can be obtained (German Pat. No. 15 41 099). By these electrical heating devices, the cooling effect obtainable by the Joule-Thomson effect can be raised or compensated more or less for the purpose of temperature control, or a warming-up can take place again after issue from the constricted gap in order to establish a suitable temperature in this manner.

Such cryosurgical instruments in which the supply duct is provided inside the discharge duct in the probe, and where an outlet nozzle is arranged at the end of the supply duct, have proved themselves in practice to be satisfactory. On the other hand, it would nevertheless be more useful to design the inner of the two coaxially arranged ducts as the discharge duct, so that the cold gas would be guided back through the inner duct, so that no additional cooling down of the probe shaft would be produced by the cold gas. In a known proposal of this kind (German Pat. No. 15 41 099), the inner discharge duct has at its end an outer flange which has such an outer diameter that between the circumference of the flange and the inner surface of the probe there is present a very small spacing or a series of spacings which are formed by irregularities of the flange and constitute a constriction. The heating winding necessary for control of the temperature can in such case be arranged adjacent to the flange of the discharge duct. Apart from the disadvantage that such devices require a current supply on account of the heating winding, it is not possible without some further provision to obtain a suitable control of the temperature because the thermal expansion or contraction of the elements which bound the gap cannot directly be controlled through current supply to the heating winding in such a way that a suitable gap size can be maintained.

SUMMARY OF THE INVENTION

It is therefore an object of the invention to improve a cryosurgical instrument of the kind mentioned in such a way that on the one hand the use of an electrical heating winding is not necessary and that on the other hand, through a more precise formation of the exit gap, the inner duct can be provided as the discharge duct. This object can be accomplished in accordance with the invention in a cryosurgical instrument of the kind mentioned in the introduction in that the discharge duct is displaceable in the axial direction relative to the supply duct that surrounds it and is externally shaped to broaden conically towards its end bounding the exit gap and a region of the inner wall of the probe bounding the exit gap extending away from the probe tip narrows conically less strongly than the conically broadened exterior of the end of the discharge duct.

The invention accordingly sets forth the recognition that it is possible within the dimension range of the necessary constriction for obtaining the Joule-Thomson effect, to adjust the exit gap during the operation of the probe in such a way that thermal expansions or contractions or deformations produced by the high overpressure can be compensated and at the same time a temperature control can result. The manufacture of such a probe can be accomplished in a more simple and more reliable manner because no narrow tolerance limits for the construction of the exit gap need to be maintained in the manufacture. It is especially advantageous for safety reasons and for reasons of construction that in the probe no supply lines for an electrical heating winding need to be provided. On the other hand, the probe tip can be thawed relatively fast in spite of the lack of the electrical heating arrangement, because for this purpose the gas present under high pressure can also be supplied to the probe tip through the discharge duct, so that the temperature of the probe tip can be sufficiently raised by condensation of the gas within a few seconds.

BRIEF DESCRIPTION OF THE DRAWINGS

The invention is to be more closely explained by way of example with reference to the drawing.

DESCRIPTION OF THE PREFERRED EMBODIMENTS

Figure 1:
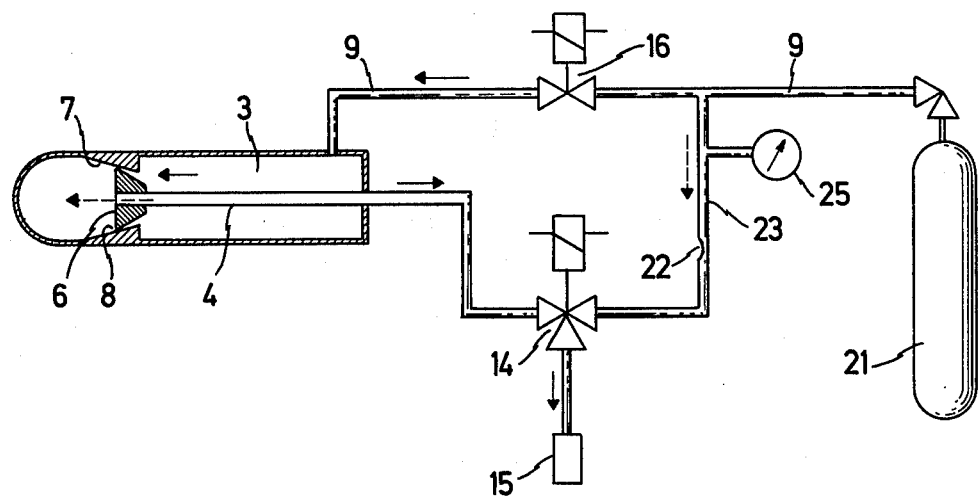
FIG. 1 shows a schematic representation of a cryosurgical instrument according to the invention.
Figure 2:
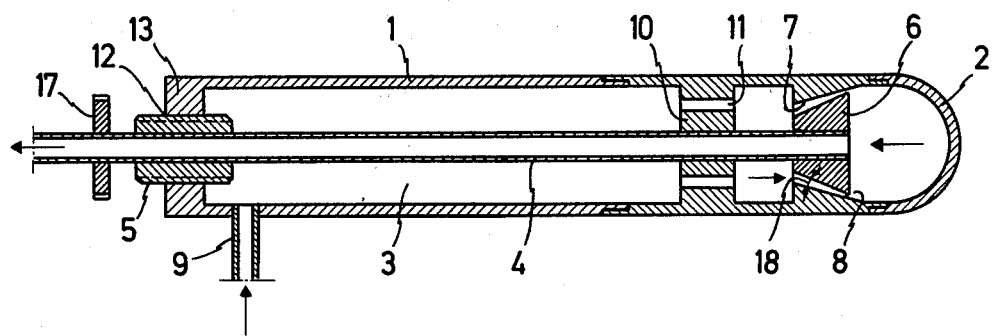
FIG. 2 shows a longitudinal section through a preferred illustrative embodiment of a probe according to the invention.

The probe 1 shown in detail and on an enlarged scale in FIG. 1 and FIG. 2 has a probe tip 2, that is preferably interchangeably fastened, so that in particular it can be replaced by a probe tip with another form of construction which requires a substantially greater cooling power.

Within a supply duct 3 a discharge duct 4 is provided. The discharge duct 4 is displaceable in the axial direction relative to the supply duct 3 that surrounds it, because in the region of the end wall 13 of the probe lying opposite the probe tip 2 there is connected with the discharge duct a threaded sleeve 5 which is set in an inner threading in the end wall 13. It is however also possible, in the region of the outer end of the threaded sleeve 5, to provide inner threading and to provide the exit duct 4 with a corresponding outer threading, whereby there can conveniently be provided along the outer circumference, in a prolongation bore of the threaded sleeve, two ring grooves for O-rings, in order to provide a seal over against the supply duct 3. Adjacent to the outer end of the threaded sleeve 5, a knurled adjusting ring 17 is mounted on the discharge duct 4. At the end of the discharge duct 4 next to the probe tip 2, the discharge duct has a conically widening exterior surface 6, of which the cone forms an exit gap 8 together with the region 7 of the inner wall of the probe that widens conically in the direction towards the probe tip, so that the effective cross-sectional area of the exit gap 8 is adjustable by axial shifting of the discharge duct 4. The discharge duct 4 is shiftably mounted between its oppositely lying ends in the probe 1 in a centering arrangement 10 having gap passage openings 11.

To supply duct 3 there is fastened a connection line 9 that is connected for example with an 8 kg bottle 21 (FIG. 1) that contains $N_2O$ (laughing gas) or $CO_2$ (carbon dioxide) in gaseous condition, under a pressure of at least 45 bar. In the supply line 9 a gas supply valve 16 is provided.

A multi-path valve 14 is connected to the discharge duct 4 through which valve the gas can be released into the open, over a sound deadener 5.

There is further connected to the connection line 9 between the valve 16 and the gas bottle 21 a conduit 23 that stands in connection with the multi-path valve 14 through a restrictor 22. A manometer 25 is also connected to this line 23.

The manner of operation is further explained as follows. After the opening of the valve of the gas bottle 21 and the opening of the valve 16, the gas flows through the connection line 9 and the supply duct 3 into the inner chamber of the probe tip 2 through the exit gap 8, in order to cool the probe tip. By adjustment of the effective size of the exit gap 8 by actuation of the adjusting ring 17, a control of the probe temperature can be produced as may be required. The angle 18 (FIG. 2) between the conical surfaces amounts for example to only 4° to 5°, so that with a relatively long path of movement of the supply duct in its rotation, a relatively small change of the effective cross-sectional area of the gap results. For this reason, there is also provided a very fine threading 12, in order to make possible a sensitive control by means of the rotation of the adjusting ring 17.

With optimal adjustment of the exit gap 8, there is produced the lowest obtainable cooling temperature of the probe tip 2. With enlargement of the exit gap 8 and also with a narrowing of the exit gap 8, there is produced a raising of the temperature of the probe tip 2 within a range of the gap size that makes possible the occurrence of the Joule-Thomson effect. Since the optimal gap size can be directly set, substantially larger cooling powers can be obtained by enlargement of the gap size, because in many cases a temperature somewhat raised above the minimum temperature can be accepted as a trade-off. On this account, interchangeable probe tips 2 can be used in connection with the probe which are of different sizes and, for example, provide a substantially larger cooling power with a substantially greater surface.

For thawing the probe tip 2, the multi-path valve 14 is switched over, while the valve 16 remains open, so that henceforth the gas subjected to high pressure also penetrates into the inner chamber of the probe tip 2 through the line 23 and the line 4 in the direction of the arrow shown in a broken line in FIG. 1, whereby the temperature of the probe tip which was at the operating temperature is raised by condensation of the high-pressure gap at the inner wall of the probe tip. The probe tip can thus be warmed relatively fast to about $-10°$ C., especially as the probe tip has a relatively small heat capacity and a heat supply also occurs from the outside. By means of an electronic timing clock, the multi-path valve 14 is switched over after, for example, 10 seconds, and the valve 16 is closed, so that then the lines involved and the probe no longer are under pressure. By a suitable construction of the coupling of the probe with the hose of the probe, it is possible for the probe to be uncoupled from the probe hose only in the pressure-free condition.

The control of the operating temperature of the probe is even simpler than the use of a heating winding for the purpose of temperature control, because after the performance of a suitable adjustment of the exit gap 8 to the minimum operating temperature of, for example, about $-80°$ C., no adjustment is in general necessary for subsequent uses, if the conditions are in other respects the same. On account of the adjustability, there is also a greater freedom of choice of the usable materials of which the probe can be made. It is practical, however, for the conical end 6 and that of the region 7 of the inner wall to consist of a material having the same thermal expansion coefficent. The conical end 6 can be soldered to the duct 4 or made integral therewith. As already mentioned, the size of the exit gap 8 is not critical in manufacture and the conically tapering introduction region ahead of the exit gap 8 is also more favorable in flow dynamics aspects than the provision of a radial flange, because vibrations of the internally disposed discharge duct could be produced by turbulence in this region. The stability of the discharge duct is further improved by the arrangement of the centering device 10 provided with gas passage openings.

I claim:

1. Cryosurgical instrument with a probe for cooling limited zones of biological tissues, including a thermally conductive probe tip having a hollow inner chamber, into which a supply duct leads through a constricted exit gap, through which duct a gas is suppliable for cooling the tip, on the basis of the Joule-Thomson effect resulting from gas flow through the exit gap, a discharge duct having first and second ends, said first end communicating with said inner chamber and said second end being open to the atmosphere, said discharge duct extending within and coaxial with respect to said supply duct, said instrument having also a valve adjustable from the outside for control of the operating temperature of the probe tip, and further comprising the improvement which consists in that said discharge duct (4) is displaceable in the axial direction relative to the supply duct (3) surrounding it, said first end of said axially movable discharge duct has a conical member arranged symmetrically around the axis of said discharge duct, with the base of said conical member facing in the direction of said inner chamber, the end of said supply duct adjoining said inner chamber having a conically tapered inner wall arranged symmetrically around the axis of the supply duct, said tapered inner wall being narrowed in the direction away from said inner chamber and said gap being formed between the edge of the base of said conical member and said inner wall of said supply duct, the size of said gap being adjustable by moving said discharge duct axially with respect to said supply duct, said conical member and said tapered inner wall being sized and positioned such that when said duct is moved axially in the direction away from said inner chamber, the edge of the base of said conical member will ultimately come in contact with the tapered inner wall of said supply duct, and said tapered inner wall narrows more strongly than the taper of said conical member.

2. Cryosurgical instrument according to claim 1 in which the angle (18) between the conical surfaces of the exterior of said discharge duct end and of said region of said inner wall, in planes tangent thereto, is smaller than 5°.

3. Cryosurgical instrument according to claim 1, in which the two respective conical portions (6,7) of the end of said discharge duct and of said region (7) of said inner wall consist of a material with the same thermal expansion coefficient.

4. Cryosurgical instrument according to claim 1, 2 or 3, in which the discharge duct (4), between its oppositely lying ends in the probe (1), is shiftably mounted in a centering device (10) having gas passage openings (11).

5. Cryosurgical instrument according to claim 1, 2, or 3, in which the supply duct (3) of the probe is connected to a gas supply line (9), in which a gas supply valve (16) is interposed, and a multipath valve (14) is provided for connecting the discharge duct (4) either for discharge to the atmosphere or for thawing the tip by reverse gas flow, a line (23) having a restrictor (22) interposed therein being provided for the latter purpose between a port of said multipath valve and a junction with said gas supply line upstream of said gas supply valve (16).

* * * * *